US012624154B2

(12) United States Patent
Pai et al.

(10) Patent No.: US 12,624,154 B2
(45) **Date of Patent: *May 12, 2026**

(54) XYLYLENEDIISOCYANATE COMPOSITION AND OPTICAL POLYMERIZABLE COMPOSITION COMPRISING SAME

(71) Applicant: SK pucore co., ltd., Ulsan (KR)

(72) Inventors: Jae Young Pai, Gyeonggi-do (KR); Jung Hwan Myung, Gyeonggi-do (KR); Kyeong Hwan You, Gyeonggi-do (KR); Hyuk Hee Han, Gyeonggi-do (KR); Jeong Moo Kim, Gyeonggi-do (KR); Eui Jun Choi, Gyeonggi-do (KR); Jung Hwan Shin, Gyeonggi-do (KR)

(73) Assignee: SK PUCORE CO., LTD., Ulsan (KR)

( * ) Notice: Subject to any disclaimer, the term of this patent is extended or adjusted under 35 U.S.C. 154(b) by 493 days.

This patent is subject to a terminal disclaimer.

(21) Appl. No.: 18/043,711

(22) PCT Filed: Sep. 2, 2021

(86) PCT No.: PCT/KR2021/011838

§ 371 (c)(1),
(2) Date: Mar. 1, 2023

(87) PCT Pub. No.: WO2022/050716

PCT Pub. Date: Mar. 10, 2022

(65) Prior Publication Data

US 2024/0294699 A1 Sep. 5, 2024

(30) Foreign Application Priority Data

Sep. 3, 2020 (KR) ........................ 10-2020-0112405

(51) Int. Cl.

| | |
|---|---|
| ***C07C 265/14*** | (2006.01) |
| ***C07C 263/18*** | (2006.01) |
| ***C07C 265/12*** | (2006.01) |
| ***C08G 18/10*** | (2006.01) |
| ***C08G 18/38*** | (2006.01) |
| ***C08G 18/76*** | (2006.01) |
| *G02B 1/04* | (2006.01) |

(52) U.S. Cl.

CPC ........ *C08G 18/7642* (2013.01); *C07C 263/18* (2013.01); *C07C 265/12* (2013.01); *C07C 265/14* (2013.01); *C08G 18/10* (2013.01); *C08G 18/3876* (2013.01); *G02B 1/04* (2013.01)

(58) Field of Classification Search

CPC .... C07C 263/18; C07C 265/12; C07C 265/14
See application file for complete search history.

(56) References Cited

U.S. PATENT DOCUMENTS

| | | | | |
|---|---|---|---|---|
| 3,914,269 | A * | 10/1975 | Nersasian | C07C 263/10 521/162 |
| 2010/0113687 | A1* | 5/2010 | Schaefer | C08K 5/005 528/72 |
| 2018/0037722 | A1* | 2/2018 | Kousaka | C08G 18/3885 |
| 2019/0225739 | A1* | 7/2019 | Miyake | C07C 263/10 |
| 2021/0163669 | A1 | 6/2021 | Shin et al. | |
| 2023/0166883 | A1* | 6/2023 | Kawaguchi | B65D 7/22 428/35.7 |

FOREIGN PATENT DOCUMENTS

| | | | | |
|---|---|---|---|---|
| EP | 3404053 | A1 | 11/2018 | |
| EP | 4209527 | A1 | 7/2023 | |
| JP | 2006273717 | A | 10/2006 | |
| JP | 4792736 | B2 | 10/2011 | |
| JP | 2019-059822 | A | 4/2019 | |
| JP | 2019-059823 | A | 4/2019 | |
| KR | 1994-0005699 | A | 3/1994 | |
| KR | 10-1142576 | B1 | 5/2012 | |
| KR | 10-2012-0076329 | A | 7/2012 | |
| KR | 10-2016-0147802 | A | 12/2016 | |
| KR | 10-1842254 | B1 | 3/2018 | |
| KR | 10-2018-0104330 | A | 9/2018 | |
| KR | 10-2018-0126356 | A | 11/2018 | |
| KR | 10-1954346 | B1 | 3/2019 | |
| KR | 10-1988494 | B1 | 6/2019 | |
| WO | WO-2005089085 | A2 * | 9/2005 | C08G 18/2815 |
| WO | WO-2021256417 | A1 * | 12/2021 | C09D 163/00 |

OTHER PUBLICATIONS

Extended European Search Report for the European Patent Application No. 21864675.0 issued by the European Patent Office on Sep. 9, 2024.
Third Party Observation for the European Patent Application No. 21864675.0 issued by the European Patent Office on Oct. 16, 2023.
Office Action for Korean Patent Application No. 10-2020-0112405 issued by the Korean Patent Office on Dec. 2, 2020.
International search report for the international application No. PCT/KR2021/011838 issued by the international searching authority on Dec. 13, 2021.

* cited by examiner

*Primary Examiner* — Michael L Leonard
(74) *Attorney, Agent, or Firm* — IP & T GROUP LLP

(57) ABSTRACT

A xylylene diisocyanate (XDI) composition according to exemplary embodiments includes xylylene diisocyanate and an acidity regulator having a boiling point of 110° C. or higher, and the composition has an acidity of greater than 100 ppm and 1,000 ppm or less based on a total weight of the xylylene diisocyanate (XDI). An optical lens having a high transmittance and improved optical uniformity can be manufactured by controlling a polymerization reaction rate through acidity adjustment.

8 Claims, No Drawings

XYLYLENEDIISOCYANATE COMPOSITION AND OPTICAL POLYMERIZABLE COMPOSITION COMPRISING SAME

This application is a national stage application of PCT/KR2021/011838 filed on Sep. 2, 2021, which claims priority to Korean Patent Application No. 10-2020-0112405 filed on Sep. 3, 2020, in the Korean Intellectual Property Office (KIPO), the entire disclosure of which is incorporated by reference herein.

CROSS-REFERENCE TO RELATED APPLICATION

This application claims priority to Korean Patent Application No. 10-2020-0112405 filed on Sep. 3, 2020 in the Korean Intellectual Property Office (KIPO), the entire disclosure of which is incorporated by reference herein.

BACKGROUND

1. Field

The present invention relates to a xylylene diisocyanate composition and an optical polymerizable composition ("polymerizable composition for an optical material") including the same. More specifically, the present invention relates to a xylylene diisocyanate composition prepared by a reaction of an amine salt, and a polymerizable composition for an optical material including the same.

2. Description of the Related Art

A diisocyanate compound is widely used, for example, as a raw material for manufacturing a polyurethane resin. For example, a diisocyanate compound is used for manufacturing an optical lens using a polyurethane resin, and physical properties of the diisocyanate compound as a manufacturing raw material may directly affect optical properties such as transparency and refractive index of the optical lens.

For example, a polythiourethane resin prepared by reacting a polythiol compound and a diisocyanate compound may be utilized as the base material of the optical lens.

Among the diisocyanate compounds, xylylene diisocyanate (XDI) is widely used in consideration of chemical and optical properties such as reactivity and transparency.

For example, a polymerizable composition for an optical lens may be prepared by preparing a composition including XDI and mixing it with a composition including a polythiol compound. In consideration of the stability of XDI and appropriate reactivity with the polythiol compound, it is necessary to design physical properties of the composition of XDI, the synthesis process and the like.

For example, Korean Patent Laid-Open Publication No. 2012-0076329 discloses a urethane-based optical material prepared using an isocyanate compound. However, physical properties of the isocyanate composition itself are not considered.

SUMMARY

An object according to exemplary embodiments is to provide a xylylene diisocyanate composition having improved reaction stability and optical properties, and a method for preparation thereof.

In addition, another object according to exemplary embodiments is to provide a polymerizable composition for an optical material which includes a xylylene diisocyanate composition having improved reaction stability and optical properties.

Further, another object according to exemplary embodiments is to provide an optical product prepared from the polymerizable composition for an optical material.

A xylylene diisocyanate composition according to exemplary embodiments includes: xylylene diisocyanate (XDI); and an acidity regulator having a boiling point of 110° C. or higher, wherein the xylylene diisocyanate composition has an acidity of greater than 100 ppm and 1,000 ppm or less based on a total weight of the xylylene diisocyanate (XDI).

In some embodiments, a chlorine content in the composition may be less than 100 ppm.

In some embodiments, the chlorine content in the composition may be 10 ppm to 95 ppm.

In some embodiments, an acidity variation of the xylylene diisocyanate composition before and after 3 months storage in a dark room at 25° C. may be 40 ppm or less.

In some embodiments, a transmittance of the xylylene diisocyanate composition to a light at 380 nm wavelength after 3 months storage in a dark room at 25° C. may be 99% or more.

In some embodiments, the acidity regulator may include at least one inorganic acid compound selected from the group consisting of halogen acids, sulfuric acid, phosphoric acid, and phosphoric acid ester-based compounds.

In some embodiments, the acidity regulator may include at least one organic acid compound selected from the group consisting of acetic acid, benzoic acid, trifluoroacetic acid (TFA), fatty acid, and aromatic carboxylic acid halide.

In some embodiments, the acidity regulator may include at least one solid acid selected from the group consisting of clay, silica alumina, cation exchange resin, acid-impregnated silica gel, acid-impregnated alumina, aluminum oxide, and vanadium oxide.

In some embodiments, the acidity regulator may include a cyclic amine compound or a tertiary amine compound.

In some embodiments, an addition amount of the acidity regulator may range from 300 ppm to 4,000 ppm.

A polymerizable composition for an optical material according to exemplary embodiments includes: a xylylene diisocyanate composition which includes xylylene diisocyanate (XDI) and an acidity regulator having a boiling point of 110° C. or higher, and has an acidity of greater than 100 ppm and 1,000 ppm or less based on a total weight of the xylylene diisocyanate (XDI); a polythiol-based compounds; and an additive.

In some embodiments, a chlorine content of the xylylene diisocyanate composition may be less than 100 ppm.

In some embodiments, the additive may include at least one selected from the group consisting of a release agent, a reaction catalyst, a thermal stabilizer, an ultraviolet absorber, and a bluing agent.

A method for preparation of a xylylene diisocyanate composition according to exemplary embodiments includes: synthesizing xylylene diisocyanate from xylenediamine to form a preliminary composition including xylylene diisocyanate; and adjusting an acidity of the preliminary composition to a range of greater than 100 ppm to 1,000 ppm.

In some embodiments, in the step of adjusting the acidity of the preliminary composition, an acidic acidity regulator may be added if the acidity of the preliminary composition is 100 ppm or less, while a basic acidity regulator is added if the acidity of the preliminary composition exceeds 1,000 ppm.

According to the above-described embodiments, the xylylene diisocyanate composition has an acidity of greater than 100 ppm and 1,000 ppm or less, and may provide improved stability and a polymerization reaction rate in an appropriate range with the polythiol-based compound.

Accordingly, an optical lens having a high transmittance and improved optical uniformity from which white turbidity and inhomogeneity ("stria") phenomena are substantially removed can be manufactured.

DETAILED DESCRIPTION OF THE EMBODIMENTS

Hereinafter, embodiments of the present application will be described in detail. In this regard, the present invention may be altered in various ways and have various embodiments, such that specific embodiments will be illustrated in the drawings and described in detail in the present disclosure. However, the present invention is not limited to the specific embodiments, and it will be understood by those skilled in the art that the present invention is to cover all modifications, equivalents, and alternatives falling within the spirit and scope of the present invention.

Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to one aspect of the present application, there is provided a composition including xylylene diisocyanate (hereinafter, may be abbreviated as an XDI composition).

According to exemplary embodiments, the XDI composition includes XDI, and may have an acidity of greater than 100 ppm and 1,000 ppm or less based on a total weight of the XDI.

The term "acidity" as used herein may be a value expressed as a ratio to the total weight of the XDI in terms of, for example, HCl in the amount of free acid component by a reaction with alcohol at room temperature.

XDI contained in the XDI composition may be reacted with a polythiol-based compound such as a trifunctional thiol compound and/or a tetrafunctional thiol compound to obtain a polythiourethane resin. According to exemplary embodiments, the acidity of the XDI composition may be adjusted as a factor affecting stability of the XDI and reactivity with the polythiol-based compound.

For example, when the acidity of the XDI composition is excessively increased, the polymerization reactivity with the polythiol-based compound may be excessively decreased. Accordingly, a process yield of the polythiourethane resin for manufacturing an optical lens may be reduced. Further, white turbidity phenomenon may be caused in a casting process for molding a lens.

When the acidity of the XDI composition is excessively decreased, polymerization reactivity with the polythiol-based compound may be excessively increased. Accordingly, instead of the desired polythiourethane resin, other by-products, for example in the form of oligomers or polymers, may be increased, which in turn, may lead to stria of the lens. Further, the self-reactivity of XDI is also increased, which may cause white turbidity phenomenon during long-term storage. Accordingly, as described below, a transmittance of the composition stock solution may be decreased when stored in a dark room for 3 months at room temperature (25° C.) for a long period of time. Further, during long-term storage, the desired target acidity may vary due to self-propagating reaction, hence causing a problem of not implementing acidity control.

In consideration of the above aspects, according to exemplary embodiments, the acidity of the XDI composition may be adjusted to greater than 100 ppm and 1,000 ppm or less. Accordingly, it is possible to maintain appropriate reactivity with the polythiol-based compound to inhibit white turbidity during lens casting and prevent stria of the lens. Further, it is possible to suppress a decrease in permeability and a variation in acidity of the XDI composition by securing the storage characteristics of the XDI composition.

In one embodiment, the acidity of the XDI composition may be 110 ppm to 800 ppm, and preferably 110 ppm to 700 ppm.

In some embodiments, the change in acidity of the XDI composition after storage in the dark at 25° C. for 3 months may be 40 ppm or less, preferably 30 ppm or less, and more preferably 20 ppm or less, or 15 ppm or less.

In addition to the acidity of the XDI composition, a chlorine content may also be adjusted. When the chlorine content in the XDI composition is increased, a yellowing phenomenon of the lens may be caused. Further, chlorine ions contained in the composition may act as an acidity variable factor.

Accordingly, when the chlorine content in the composition is increased, the acidity of the composition adjusted to a predetermined range is changed as described above, and thus the acidity of the desired target range may not be easily implemented. In addition, when the composition is stored for a long time, the acidity is altered due to chlorine, such that desired properties of the lens may not be obtained.

In some embodiments, the chlorine content in the XDI composition may be less than 100 ppm. Preferably, the chlorine content in the XDI composition may be 95 ppm or less.

In one embodiment, the chlorine content in the XDI composition may be maintained at 10 ppm or more and less than 100 ppm. In this case, it is possible to prevent excessive increase in process load in distillation and purification processes of the XDI composition and to stably maintain the chlorine content in the corresponding range. In one embodiment, the chlorine content in the XDI composition may be maintained in a range of 10 ppm to 95 ppm, 10 ppm to 80 ppm, and preferably 30 ppm to 80 ppm or 40 ppm to 80 ppm.

According to exemplary embodiments, an acidity regulator for finely adjusting the acidity within the above-described range may be added to the XDI composition, and a compound having a boiling point of 110° C. or higher may be used as the acidity regulator.

As the acidity regulator having a boiling point of 110° C. or higher is used, a change in content of the acidity regulator during the distillation process in the XDI composition manufacturing process may be inhibited. Therefore, it is possible to stably maintain the acidity and chlorine content in the above-described ranges. Further, using an acidity regulator having a high boiling point may inhibit side reactions caused by the acidity regulator, improve long-term storage of the XDI composition, and maintain a desired acidity range for a long period of time.

In some embodiments, a transmittance of the XDI composition to 380 nm wavelength light after 3 months storage in a dark room at 25° C. may be 99% or more.

The acidity regulator may include an inorganic acid compound, an organic acid compound, or a solid acid.

Examples of the inorganic acid compound may include halogen acids such as hydrochloric acid, hydrobromic acid and iodic acid, sulfuric acid, phosphoric acid, and phosphoric acid-based derivatives.

In one embodiment, the phosphoric acid-based derivative may include a phosphoric acid ester-based compound such as a phosphate-based compound or a phosphonate-based compound. For example, the phosphoric acid-based derivative may include a compound of Formula 1 below.

[Formula 1]

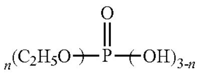

In Formula 1, n is 1 or 2.

Examples of the organic acid compound may include acetic acid, benzoic acid, formic acid, trifluoroacetic acid (TFA), fatty acid, aromatic carboxylic acid halide (e.g., benzoyl halide, phenylacetyl halide, phthaloyl halide, terephthaloyl halide, isophthaloyl halide) and the like.

Examples of the solid acid may include acid clay, silica alumina, a cation exchange resin, acid-impregnated silica gel, or a solid acid such as alumina, aluminum oxide, or vanadium oxide.

In some embodiments, the acidity regulator may include a basic compound that is not substantially reactive with XDI. For example, the acidity regulator may include a cyclic amine such as imidazole, tetrazole, pyridine, or the like, or a tertiary amine such as N,N-dimethylaniline ($PhNMe_2$).

In some embodiments, an addition amount or content of the acidity regulator may be adjusted in consideration of the above-described acidity range and chlorine content, for example, 300 ppm to 4,000 ppm, and preferably 400 ppm to 3,500 ppm, or 500 ppm to 3,000 ppm.

In one embodiment, XDI content in the XDI composition may be 90% by weight ("wt. %") or more, 95 wt. % or more or 99 wt. % or more, and for example, 99 wt. % or more to less than 100 wt. %. In one embodiment, the acidity regulator may be added within a range capable of obtaining acidity in the above-described range.

According to exemplary embodiments, there is provided a method for preparing an XDI composition, which includes the following steps, processes or actions.

The method for preparing an XDI composition according to exemplary embodiments may include at least one of the steps, processes, or actions described as S10 and S20 below. It should be understood that the following terms "S10" and "S20" are used to distinguish processes for the convenience of description and are not intended to limit the sequential order thereof. For example, some or all of the processes of S10 and S20 below may be sequentially conducted, and/or may be conducted with altered order according to process conditions.

S10) Obtaining a preliminary composition containing XDI through an XDI synthesis process.

S20) Checking an acidity of the preliminary composition, and if the composition has an acidity of 100 ppm or less or greater than 1,000 ppm, adjusting the acidity to obtain an XDI composition having an acidity of greater than 100 ppm and 1,000 ppm or less.

For example, xylylene diisocyanate (XDI) may be synthesized from xylylene diamine in step (S10).

In some embodiments, XDI may be synthesized from xylylenediamine through a phosgene method. For example, xylylenediamine may be reacted with concentrated hydrochloric acid in a solvent to produce an amine salt. XDI may be synthesized by reacting the amine salt with phosgene ($COCl_2$) (see Scheme 1 below).

[Scheme 1]

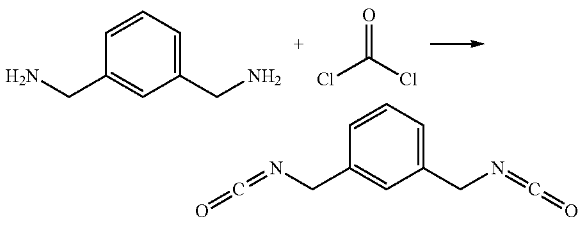

In some embodiments, XDI may be synthesized from xylylenediamine through a non-phosgene method. For example, xylylenediamine may be reacted with concentrated hydrochloric acid to produce an amine salt. The amine salt may be reacted with a halodialkyl carbonate to produce a biscarbamate. XDI may be synthesized by thermally degrading or degassing the biscarbamate in the presence of a catalyst (see Scheme 2 below).

[Scheme 2]

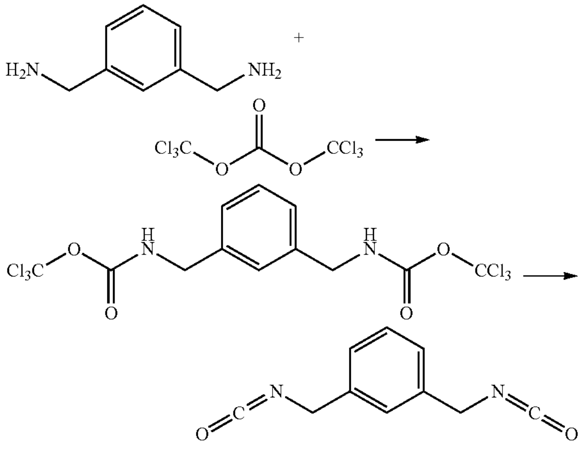

As shown in Scheme 2, bis(trichloromethyl)carbonate (BTMC) may be used as an example of the halodialkyl carbonate.

For example, a first solution in which the amine salt is dissolved in an inert solvent may be prepared, and a second solution in which the halodialkyl carbonate is dissolved in an inert solvent may be prepared. The biscarbamate synthesis reaction may proceed while adding the second solution dropwise to the first solution into a reactor. A temperature in the reactor may be maintained, for example, in a range of about 120° C. to 150° C.

Thereafter, a degassing process may be conducted by feeding an inert gas to the reaction solution while maintaining the temperature in the above range. Then, the reaction solution may be cooled, followed by filtering and drying thus to obtain an XDI composition.

In some embodiments, a distillation process may be further conducted to remove the inert solvent and take out XDI. For example, a first distillation for removing the inert solvent and a second distillation for taking out XDI may be sequentially performed.

A first distillation temperature may be appropriately adjusted according to the boiling point of the inert solvent. The second distillation may be conducted at a second distillation temperature, for example, at a temperature greater than or equal to the boiling point of XDI.

In some embodiments, the first distillation temperature may be 100° C. or less, for example, in a range of 50° C. to 90° C., and preferably 50° C. to 80° C. Meanwhile, the second distillation temperature may be 115° C. or higher, for example, in a range of 120° C. to 150° C., and preferably 120° C. to 140° C.

The first distillation and the second distillation may be conducted under a pressure condition of 1 torr or less, and preferably at a pressure condition of 0.5 torr or less.

The inert solvent may include an organic solvent that is not substantially reactive with the amine salt, XDI and the halodialkyl carbonate. Further, an organic solvent having a lower boiling point than XDI may be used for conducting the above-described distillation process.

In one embodiment, the inert solvent may include chlorinated aromatic hydrocarbon, for example, monochlorobenzene, dichlorobenzene, trichlorobenzene, chloroethylbenzene and the like.

According to exemplary embodiments, the acidity of the XDI-containing preliminary composition prepared as described above in step S20 is measured, and if it has an acidity of 100 ppm or less or greater than 1,000 ppm, the preliminary composition may be adjusted to have an acidity of greater than 100 ppm and 1,000 ppm or less.

When the acidity of the preliminary composition is 100 ppm or less, an acidic acidity regulator may be added. The acidic acidity regulator may include the above-described inorganic acid compound, organic acid compound, or solid acid.

Preferably, in consideration of fine acidity control, a liquid organic acid compound may be used.

When the acidity of the preliminary composition exceeds 1,000 ppm, the above-described basic compound may be added.

In some embodiments, when the acidity of the preliminary composition is greater than 100 ppm and 1,000 ppm or less, the preliminary composition may be used as the XDI composition without addition of an acidity regulator.

According to one aspect of the present application, there is provided a polymerizable composition for an optical material including the XDI composition prepared as described above.

The polymerizable composition for an optical material may include a polythiol-based compound and the XDI composition.

The polythiol-based compound may include a trifunctional polythiol compound and/or a tetrafunctional polythiol compound.

A non-limiting example of the trifunctional polythiol compound may include a compound represented by Formula 1 below.

[Formula 1]

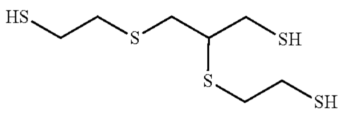

The trifunctional polythiol compound may be synthesized from, for example, a polyol compound obtained through a reaction with 2-mercaptoethanol and epihalohydrin.

After the polyol compound is reacted with thiourea under acidic conditions to produce a thiuronium salt, a trifunctional polythiol compound may be prepared through hydrolysis under basic conditions.

Non-limiting examples of the tetrafunctional polythiol compound may include compounds represented by Formulae 2-1 to 2-3 below.

[Formula 2-1]

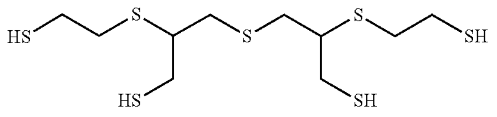

[Formula 2-2]

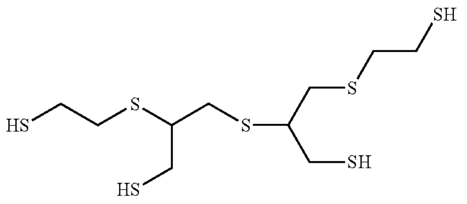

[Formula 2-3]

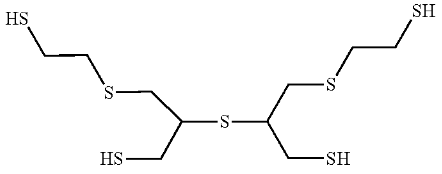

The tetrafunctional polythiol compound may be synthesized from, for example, a polyol compound obtained through a reaction with 2-mercaptoethanol and epihalohydrin. The polyol compound may be reacted with a metal sulfide to produce a tetrafunctional polyol intermediate. After the tetrafunctional polyol intermediate is reacted with thiourea under acidic conditions to produce a thiuronium salt, a tetrafunctional polythiol compound may be prepared by hydrolysis under basic conditions.

The polymerizable composition for an optical material may further include additives such as a release agent, a reaction catalyst, a thermal stabilizer, an ultraviolet absorber, a bluing agent and the like.

Examples of the release agent may include a fluorine-based nonionic surfactant having a perfluoroalkyl group, a hydroxyalkyl group or a phosphoric acid ester group; a silicone-based nonionic surfactant having a dimethylpolysiloxane group, a hydroxyalkyl group or a phosphoric acid ester group; alkyl quaternary ammonium salts such as trimethylcetyl ammonium salt, trimethylstearyl, dimethylethylcetyl ammonium salt, triethyldodecyl ammonium salt, trioctylmethyl ammonium salt and diethylcyclohexadodecyl ammonium salt; acidic phosphoric acid ester and the like. These may be used alone or in combination of two or more thereof.

As the reaction catalyst, a catalyst used in the polymerization reaction of the polythiourethane resin may be used. For example, dialkyltin halide catalysts, such as dibutyltin dichloride and dimethyltin dichloride; dialkyltin dicarboxylate catalysts such as dimethyltin diacetate, dibutyltin dioctanoate, and dibutyltin dilaurate; dialkyltin dialkoxide catalysts such as dibutyltin dibutoxide and dioctyltin dibutoxide; dialkyltin dithio alkoxide catalysts such as dibutyltin di(thiobutoxide); dialkyltin oxide catalysts such as di(2-ethylhexyl)tin oxide, dioctyltin oxide, and bis(butoxydibutyltin) oxide; dialkyltin sulfide catalysts, and the like may be used. These may be used alone or in combination of two or more thereof.

As examples of the ultraviolet absorber, benzophenone-based, benzotriazole-based, salicylate-based, cyanoacrylate-based, oxanilide-based compounds, and the like may be used. As examples of the thermal stabilizer, metal fatty acid salt-based, phosphorus-based, lead-based, organotin-based compounds, and the like may be used. These may be used alone or in combination of two or more thereof.

The bluing agent may be included as a color control agent of the optical material prepared from the polythiourethane resin. For example, the bluing agent may have an absorption band in a wavelength band from orange to yellow in a visible light region.

Examples of the bluing agent may include a dye, a fluorescent whitening agent, a fluorescent pigment, an inorganic pigment, and the like, and may be appropriately selected according to physical properties or resin color required for the optical product to be manufactured. When a dye is used as the bluing agent, for example, a dye having a maximum absorption wavelength of 520 nm to 600 nm, and preferably 540 nm to 580 nm may be used. Preferably, anthraquinone-based dyes may be used.

In some embodiments, based on a total weight of the polymerizable composition for an optical material, the polythiol-based compound may be included in a content of about 40 wt. % to 60 wt. % and the isocyanate-based compound may be included in a content of about 40 wt. % to 60 wt. %, while the additive may be included in a content of about 0.01 wt. % to 1 wt. %.

A polythiourethane resin may be produced through a polymerization reaction of the polythiol-based compound and XDI included in the polymerizable composition for an optical material.

As described above, the acidity of the XDI composition used in the polymerizable composition for an optical material is adjusted to be greater than 100 ppm and 1,000 ppm or less, such that the reactivity with the polythiol-based compound or a reaction rate thereof may be appropriately controlled. Thereby, while inhibiting a white turbidity phenomenon derived from the XDI composition itself, the white turbidity phenomenon in an optical lens manufactured using the polymerizable composition for an optical material may also be prevented.

In some embodiments, a reaction rate of the polymerizable composition for an optical material involved in Equation 1 to be described below may be maintained in a range of 0.17 to 0.30 by the reaction regulator. The reaction rate may be maintained in a range of 0.17 to 0.25, and preferably 0.19 to 0.21.

Further, through stable polymerization reaction, an optical lens having uniform refractive index without stria phenomenon may be produced.

According to one aspect of the present application, an optical product manufactured using the above-described polymerizable composition for an optical material may be provided.

For example, after degassing the polymerizable composition for an optical material under reduced pressure, the resultant composition may be injected into a mold for molding an optical material. Mold injection may be performed, for example, in a temperature range of 10° C. to 40° C., and preferably 10° C. to 30° C.

After the mold injection, the temperature may be gradually increased to proceed with the polymerization reaction of the polythiourethane resin. The polymerization temperature may range from 20° C. to 150° C., and preferably 25° C. to 125° C. For example, the maximum polymerization temperature may range from 100° C. to 150° C., preferably 110° C. to 140° C., and more preferably 115° C. to 130° C.

The polymerization time may be 1 to 10 hours, and preferably from 1 to 5 hours.

For example, a lens having uniform optical properties and mechanical properties can be easily obtained by appropriately controlling the reaction rate within the above temperature range.

After completion of polymerization, the polymerized polythiourethane resin may be separated from the mold to obtain an optical product. The optical product may be manufactured in the form of a spectacle lens, a camera lens, a light emitting diode, etc. according to a shape of the mold.

In one embodiment, after separation from the mold, a curing process may be further conducted. The curing process may be conducted in a range of 100° C. to 150° C., preferably 110° C. to 140° C., and more preferably 115° C. to 130° C. for about 1 to 10 hours, and preferably 1 to 3 hours.

The refractive index of the optical product may be adjusted according to the type and/or content ratio of the polythiol-based compound and the isocyanate-based compound used in the polymerizable composition for an optical material. For example, the refractive index of the optical product may be adjusted in a range of 1.56 to 1.78, 1.58 to 1.76, 1.60 to 1.78, or 1.60 to 1.76, and preferably in a range of 1.65 to 1.75 or 1.69 to 1.75.

A color index (yellowness index (YI)) of the optical product according to Equation 2 which will be described below may be less than 30, preferably 28 or less, and more preferably 22 or less, or 21 or less.

The optical product may be improved by further conducting surface treatment such as anti-fouling, color imparting, hard coat, surface polishing, hardness strengthening and the like.

Hereinafter, embodiments provided in the present application will be further described with reference to specific experimental examples. However, the following experimental examples only illustrate the present invention and are not intended to limit the appended claims, and those skilled in the art will obviously understand that various alterations and modifications are possible within the scope and spirit of the present invention. Such alterations and modifications are duly included in the appended claims.

Preparative Examples (1) Preparation of Xylenediamine (XDA) Hydrochloric Acid Salt 1009.4 g (9.46 mol) of a 35% hydrochloric acid solution was introduced into a reactor, and the reactor was cooled to decrease an internal temperature to a range of 15 to 20° C. while stirring. Then, 600.0 g (4.4 mol) of meta-xylylenediamine (m-XDA) was slowly added while maintaining the reactor temperature in a range of 20 to 60° C.

After completion of m-XDA input, the reactor was cooled to decrease the internal temperature to a range of 10 to 20° C. and, after stirring for 1 hour, 1,320.0 g of tetrahydrofuran was added. Then, the reactor was cooled again to decrease the internal temperature to a range of −5 to 0° C., and the reaction was allowed to proceed along with additional stirring for 1 hour.

After completion of the reaction, vacuum filtration was conducted, followed by drying at an external temperature outside the reactor in a range of 90 to 100° C. and under a condition of a vacuum pump of 0.1 torr to remove residual solvent and moisture, thereby obtaining m-XDA hydrochloride.

(2) Preparation of Xylylene Diisocyanate Composition 800 g of m-XDA hydrochloride prepared in the above 1) and 3,550 g of ortho-diclobenzene (ODCB) were introduced into the reactor, and the reactor was heated to increase the internal temperature to about 125° C. while stirring.

950 g of bis(trichloromethyl) carbonate (BTMC) and 800 g of ODCB were dissolved while stirring at about 60° C., and then the reactor temperature was dropped to 125° C. over 24 hours so as to prevent precipitation. After the end of dropping, pre-mixing was conducted for 4 hours.

After completion of the reaction, $N_2$ gas was fed to the reaction solution at a temperature of 125° C., followed by a degassing process while bubbling. After the degassing reaction solution was cooled to 10° C., the remaining solids were filtered using Celite 545.

The filtered organic solvent and the synthesized crude XDI were purified by distillation under the following conditions.

1) Removal of organic solvent (ODCB) (first distillation)
 Vacuum: 0.5 torr or less
 Distillation column bottom temperature: 60° C.
 Distillation time: 8 hours 2) XDI distillation (second distillation)
 Vacuum: 0.5 torr or less
 Distillation column bottom temperature: 120° C.
 Distillation time: 10 hours Each of XDI compositions according to the examples and comparative examples was prepared by adding an acidity regulator to the XDI prepared as described above to measure the acidity as shown in Table 1 below. Specifically, the acidity of the prepared preliminary composition containing XDI was first measured, and the acidity regulator was added so that a target acidity shown in Table 1 was obtained, while measuring the acidity, resulting in the XDI composition as prepared above.

In the case of Comparative Examples 2, 3 and 8, the acidity and chlorine content were varied by changing the second distillation temperature. In the case of Comparative Examples 2 and 8, the second distillation temperature was altered to 180° C. and 170° C., respectively, and the second distillation temperature of Comparative Example 3 was adjusted to 120° C.

Method of Measuring Acidity 20 g of the prepared XDI composition sample was quantified and introduced into a 200 ml beaker, 100 ml of a solvent (acetone and ethanol mixed in a 1:1 weight ratio) was added thereto and heated on a hot plate to dissolve the sample, followed by mixing the solution at room temperature for 10 to 20 minutes.

Then, using an automatic measurement device (Hiranuma COM-500), in accordance with JIS K4101, acidity was calculated according to the following equation, such that a solution (N/100 methanolic potassium hydroxide solution) prepared by diluting 0.1 mol/L methanolic potassium hydroxide adjusted and expressed using methanol was used to form a titration curve, and a rising point of the curve was used as the endpoint.

$$\text{Acidity} = 0.0365 \times (A - B) \times f/S$$

A: Amount (ml) of N/100 methanolic potassium hydroxide solution required for titration of the sample
B: Amount (ml) of N/100 methanolic potassium hydroxide solution required for blank test
f: Factor of N/100 methanolic potassium hydroxide solution
S: Weight (g) of sample 2) Preparation of Polymerizable Composition for an Optical Material and Lens 49.3 parts by weight ("wt. parts") of 4,8-bis(mercaptomethyl)-3,6,9-trithiaundecane-1,11-dithiol as a polythiol compound, 50.7 wt. parts of xylylene diisocyanate synthesized according to the above preparative example, 0.01 wt. parts of dibutyltin chloride, and 0.1 wt. parts of phosphoric acid ester release agent produced by ZELEC® UN Stepan were uniformly mixed, followed by conducting a defoaming process at 600 Pa for 1 hour, thereby preparing a polymerizable composition for an optical material.

The resin composition filtered through a 3 μm Teflon filter was injected into a mold including a glass mold and a tape. After maintaining the mold at 10 to 25° C. for 8 hours, the temperature was slowly increased to 130° C. for 8 hours at a constant rate, and polymerization was performed at 130° C. for 2 hours. After the polymerization was completed, the mold was separated and the product was further cured at 120° C. for 2 hours to produce a lens sample.

Experimental Examples (1) Measurement of Chlorine Content

A chlorine content in each of the XDI compositions of the examples and comparative examples was measured using a sample combustion apparatus (Analytech/AQF-2100H, Mitsubishi Chemical) and ion chromatography (881 Compact IC Pro, metrohm).

(2) Measurement of Acidity Variation

After storing each of the XDI compositions of the examples and comparative examples in a dark room at 25° C. for 3 months, acidity was measured by the above-described method. A variation in acidity was calculated using the measured values of acidity before and after storage in the dark.

(3) Evaluation of White Turbidity of XDI Composition

After storing each of the XDI compositions of the examples and comparative examples in a dark room at 25° C. for 3 months, a sample was placed in a 10 mm quartz cell and a transmittance was measured at a wavelength of 380 nm and at 25° C. (Transmittance measuring equipment: Lambda 365, Perkinelmer Co.)

(4) Evaluation of Physical Properties of Polymerizable Composition/Lens

1) Evaluation of Stria

As described above, a lens sample having a diameter of 75 mm and −8.00D was prepared using the polymerizable composition according to each of the examples and comparative examples. Then, a light from a mercury lamp light source was transmitted through the prepared lens sample, and the transmitted light was projected on a white plate in order to determine the presence or absence of stria based on the presence or absence of contrast. Standards for evaluation are as follows.

○: Stria not observed
Δ: Fine partial stria observed
x: Stria clearly observed visually 2) Evaluation of White Turbidity of Lens For the lens samples of the examples and comparative examples prepared as described above, each sample was irradiated with right beams from a projector in a dark room, and it was visually confirmed whether the lens had haze or an opaque material.

Standards for evaluation are as follows.

○: No haze

Δ: Partial haze observed x: Haze clearly observed as a whole

3) Measurement of Polymerization Reaction Rate (Reactivity Slope)

Using a non-contact viscometer of EMS-1000 (KEM), the standard viscosity (Standard cps) was first confirmed with a viscosity standard solution (Brookfield, 1000 cps, 25° C.). Thereafter, the viscosity was measured at 10° C. for 24 hours for the polymerizable compositions according to the examples and comparative examples, respectively. Using the measured values, mathematical formulation ("mathematization") was conducted with an X-axis as a time and a Y-axis as a viscosity while converting the Y-axis in a logarithmic scale as shown in Equation 1 below, and then the reaction rate was derived therefrom.

$$Y = a \times \exp(b \times X) \quad \text{[Equation 1]}$$

In Equation 1, 'a' value represents an initial viscosity (cps) while 'b' value represents the reaction rate, the measured value was expressed by rounding to the two decimal places of the measured value.

4) Measurement of Color Index (Yellow Index (YI))

For the lens samples of the examples and comparative examples, YI was measured respectively using UV/VIS Spectroscopy (PerkinElmer, Model UV/VIS Lambda 365). Specifically, the chromaticity coordinates x and y were measured by transmitting light in a height direction of a plastic circumference (r (radius)×H (height)=16 mm×45 mm). YI was calculated by Equation 2 below based on the measured values of x and y.

$$YI = (234 \times x + 106 \times y + 106)/y \quad \text{[Equation 2]}$$

Measurement results and evaluation results are shown together in Tables 1 and 2 below.

TABLE 1

| | XDI composition acidity (ppm) | Type of acidity regulator | Added amount of acidity regulator | Boiling point of acidity regulator (° C.) | Chlorine content (ppm) |
|---|---|---|---|---|---|
| Example 1 | 115 | E | 1000 | 249 | 45 |
| Example 2 | 228 | E | 2000 | 198 | 51 |
| Example 3 | 133 | G | 500 | 158 | 67 |
| Example 4 | 296 | G | 1000 | 158 | 58 |
| Example 5 | 120 | H | 1000 | 118 | 55 |
| Example 6 | 243 | H | 2000 | 118 | 62 |
| Example 7 | 234 | I | 1000 | 203 | 78 |
| Example 8 | 780 | I | 3000 | 203 | 76 |
| Example 9 | 125 | D | 500 | 225 | 125 |
| Example 10 | 222 | D | 1000 | 225 | 241 |
| Example 11 | 185 | C | 1000 | 198 | 286 |

TABLE 1-continued

| | XDI composition acidity (ppm) | Type of acidity regulator | Added amount of acidity regulator | Boiling point of acidity regulator (° C.) | Chlorine content (ppm) |
|---|---|---|---|---|---|
| Comparative Example 1 | 29 | C | 200 | 198 | 86 |
| Comparative Example 2 | 1025 | — | — | — | 1366 |
| Comparative Example 3 | 72 | — | — | — | 90 |
| Comparative Example 4 | 527 | A | 1000 | 69 | 135 |
| Comparative Example 5 | 279 | B | 1000 | 60 | 223 |
| Comparative Example 6 | 108 | F | 1000 | 101 | 43 |
| Comparative Example 7 | 225 | F | 2000 | 101 | 42 |
| Comparative Example 8 | 942 | — | — | — | 1215 |

Specific compounds of the acidity regulator used in Table 1 are as follows.

A: Sulfuryl chloride

B: Trimethylsilyl chloride

C: Benzoyl chloride

D: Phenylacetyl chloride

E: Benzoic acid

F: Formic acid

G: Phosphoric acid

H: Acetic acid

I: Ethyl acid phosphate

TABLE 2

| | Acidity after storage at 25° C. | | Transmittance after storage at 25° C. | Physical properties of lens | | | |
|---|---|---|---|---|---|---|---|
| | for 3 months (ppm) | Acidity variation (ppm) | for 3 months (%) | Stria | White turbidness | Reaction rate (b) | YI |
| Example 1 | 114 | 1 | >99 | ○ | ○ | 0.21 | 20 |
| Example 2 | 215 | 13 | >99 | ○ | ○ | 0.20 | 20 |
| Example 3 | 125 | 8 | >99 | ○ | ○ | 0.21 | 21 |
| Example 4 | 289 | 7 | >99 | ○ | ○ | 0.19 | 21 |
| Example 5 | 102 | 18 | >99 | ○ | ○ | 0.21 | 21 |
| Example 6 | 211 | 32 | >99 | ○ | ○ | 0.20 | 21 |
| Example 7 | 225 | 9 | >99 | ○ | ○ | 0.20 | 20 |
| Example 8 | 768 | 12 | >99 | ○ | ○ | 0.17 | 22 |
| Example 9 | 110 | 15 | >99 | ○ | ○ | 0.21 | 26 |
| Example 10 | 202 | 20 | >99 | ○ | ○ | 0.21 | 28 |
| Example 11 | 178 | 7 | >99 | ○ | ○ | 0.21 | 26 |
| Comparative Example 1 | 28 | 1 | 57 | x | ○ | 0.24 | 23 |
| Comparative Example 2 | 953 | 72 | >99 | ○ | x | 0.14 | 28 |
| Comparative Example 3 | 66 | 6 | 68 | x | ○ | 0.26 | 20 |
| Comparative Example 4 | 338 | 189 | >99 | ○ | ○ | 0.18 | 30 |
| Comparative Example 5 | 125 | 154 | >99 | ○ | ○ | 0.19 | 30 |
| Comparative Example 6 | 45 | 63 | 77 | Δ | ○ | 0.23 | 20 |
| Comparative Example 7 | 68 | 157 | 88 | x | ○ | 0.24 | 20 |
| Comparative Example 8 | 899 | 43 | >99 | ○ | Δ | 0.16 | 30 |

Referring to Tables 1 and 2, it was found that, in the examples with an acidity of greater than 100 ppm and 1000 ppm or less, white turbidity in the composition and lens state was prevented, an appropriate polymerization reaction rate was obtained, and lens stria were inhibited. Further, as an acidity regulator, a compound with a boiling point of 110° C. or higher was added to inhibit the variation in acidity during long-term storage, and the composition permeability was also improved.

Referring to Examples 1 to 8, the chlorine content in the composition was reduced to less than 100 ppm, such that yellowing of the lens was decreased and stria due to an increase in the reaction rate was more efficiently suppressed.

What is claimed is:

1. A xylylene diisocyanate composition, comprising: xylylene diisocyanate (XDI); and an acidity regulator,
- wherein the xylylene diisocyanate composition has an acidity of greater than 100 ppm and 1,000 ppm or less based on a total weight of the xylylene diisocyanate (XDI),
  - wherein a chlorine content of the xylylene diisocyanate composition is less than 100 ppm,
  - wherein the chlorine content of the xylylene diisocyanate composition is measured using a sample combustion apparatus and ion chromatography, and
  - wherein the acidity regulator comprises at least one compound selected from the group consisting of:
    - an inorganic acid compound including halogen acids, sulfuric acid and phosphoric acid;
    - an organic acid compound including trifluoroacetic acid (TFA) and fatty acid;
    - a solid acid including clay, cation exchange resin, acid-impregnated silica gel, acid-impregnated alumina and vanadium oxide;
    - a cyclic amine compound; and
    - a tertiary amine compound, and
  - wherein an acidity variation before and after 3 months storage of the xylylene diisocyanate composition in a dark room at 25° C. is 40 ppm or less.

2. The xylylene diisocyanate composition according to claim 1, wherein the chlorine content in the xylylene diisocyanate composition is 10 ppm to 95 ppm.

3. The xylylene diisocyanate composition according to claim 1, wherein a transmittance to a light at 380 nm wavelength after 3 months storage in a dark room at 25° C. is 99% or more.

4. The xylylene diisocyanate composition according to claim 1, wherein an addition amount of the acidity regulator ranges from 300 ppm to 4,000 ppm.

5. A polymerizable composition for an optical material, comprising:
- a xylylene diisocyanate composition according to claim 1;
- a polythiol-based compounds; and
- an additive.

6. The polymerizable composition for an optical material according to claim 5, wherein the additive includes at least one selected from the group consisting of a release agent, a reaction catalyst, a thermal stabilizer, an ultraviolet absorber, and a bluing agent.

7. A method for preparation of a xylylene diisocyanate composition, the method comprising:
- synthesizing xylylene diisocyanate from xylenediamine to form a preliminary composition including xylylene diisocyanate;
- adjusting an acidity of the preliminary composition to a range of greater than 100 ppm to 1,000 ppm based on a total weight of the xylylene diisocyanate by using an acidity regulator,
  - wherein the xylylene diisocyanate composition is prepared to have a chlorine content of less than 100 ppm by changing a distillation temperature of the xylylene diisocyanate composition in the synthesizing, and
  - wherein the chlorine content of the xylylene diisocyanate composition is measured using a sample combustion apparatus and ion chromatography,
  - wherein the acidity regulator comprises at least one compound selected from the group consisting of:
    - an inorganic acid compound including halogen acids, sulfuric acid and phosphoric acid;
    - an organic acid compound including trifluoroacetic acid (TFA) and fatty acid;
    - a solid acid including clay, cation exchange resin, acid-impregnated silica gel, acid-impregnated alumina and vanadium oxide;
    - a cyclic amine compound; and
    - a tertiary amine compound, and
  - wherein an acidity variation before and after 3 months storage of the xylylene diisocyanate composition in a dark room at 25° C. is 40 ppm or less.

8. The method according to claim 7, wherein, in the step of adjusting the acidity of the preliminary composition, the acidity regulator which is an acidic acidity regulator is added if the acidity of the preliminary composition is 100 ppm or less, while the acidity regulator which is a basic acidity regulator is added if the acidity of the preliminary composition exceeds 1,000 ppm.

* * * * *